US012678544B2

(12) United States Patent
Chen

(10) Patent No.: US 12,678,544 B2
(45) Date of Patent: Jul. 14, 2026

(54) BREAST PUMP

(71) Applicant: SHENZHENSHI LUTEJIACHENG SUPPLYCHAIN MANAGEMENT CO., LTD., Shenzhen City (CN)

(72) Inventor: Wanyuan Chen, Shenzhen City (CN)

(73) Assignee: SHENZHENSHI LUTEJIACHENG SUPPLYCHAIN MANAGEMENT CO., LTD., Shenzhen (CN)

( * ) Notice: Subject to any disclaimer, the term of this patent is extended or adjusted under 35 U.S.C. 154(b) by 637 days.

(21) Appl. No.: 18/141,425

(22) Filed: Apr. 30, 2023

(65) Prior Publication Data

US 2024/0001010 A1 Jan. 4, 2024

Related U.S. Application Data

(63) Continuation-in-part of application No. 17/962,556, filed on Oct. 10, 2022, now Pat. No. 12,576,193.

(30) Foreign Application Priority Data

Jul. 4, 2022 (CN) .......................... 202221735508.2

(51) Int. Cl.
    *A61M 1/06* (2006.01)

(52) U.S. Cl.
    CPC ................................... *A61M 1/062* (2014.02)

(58) Field of Classification Search
    CPC ............................................ A61M 1/06–0697
    See application file for complete search history.

(56) References Cited

U.S. PATENT DOCUMENTS

| | | | | |
|---|---|---|---|---|
| 11,554,198 B1* | 1/2023 | Pan | ....................... | A61M 1/062 |
| 11,554,199 B1 | 1/2023 | Chen | | |
| 11,806,454 B2 | 11/2023 | De Becdelievre et al. | | |
| 2014/0094748 A1* | 4/2014 | Hong | .................... | A61M 1/062 |
| | | | | 604/74 |
| 2015/0217034 A1 | 8/2015 | Pollen et al. | | |
| 2016/0296682 A1* | 10/2016 | Phillips | ................. | A61M 1/067 |
| 2022/0265907 A1* | 8/2022 | Hwang | ................. | A61M 1/067 |

\* cited by examiner

*Primary Examiner* — Courtney Fredrickson

(57) ABSTRACT

A breast pump includes a milk bowl, a breast shield, a main body, and a membrane. The breast shield is detachably connected to the milk bowl. A milk storage cavity for storing milk is defined by the breast shield and the milk bowl. The main body is detachably connected to the milk bowl. The breast shield has a flange shaped to fit a breast and a milk pumping channel for receiving a nipple. An air pump for generating negative pressure is provided inside the main body, the milk bowl is air communicated with the negative pressure generated by the air pump and acting on the milk pumping channel to promote lactation. The membrane prevents the milk from reaching the air pump. The milk bowl is provided with a connecting part connected with the membrane, and the connecting part is embedded in the membrane.

21 Claims, 13 Drawing Sheets

100

300

211

200

210

218

262

260

261

A

BREAST PUMP

FIELD OF THE DISCLOSURE

The present disclosure relates to the technical field of breast pumps, and more particularly to a breast pump.

BACKGROUND OF THE DISCLOSURE

The breast pump is used to assist lactating women to pump the milk in the breast and store the milk in a milk collector, so as to solve the problem of breastfeeding for lactating women. The breast pump is mainly composed of a milk bowl and a main body. A vacuum pump in the main body can provide negative pressure for the milk collector so that the milk bowl can pump the milk in the breast.

However, during the working process of the existing breast pump, the membrane is easily pushed away from the ventilation place in the vacuum pump by the air pressure, causing air leakage and affecting the use of the breast pump.

SUMMARY OF THE DISCLOSURE

The purpose of the present disclosure is to provide a breast pump for the defects and deficiencies of the prior art, which has the advantage that the membrane can be firmly assembled in the milk bowl, and is not easy to be pushed away from the ventilation place in the vacuum pump by the air pressure.

For achieving the aforementioned purpose, the technical solution adapted by the present disclosure is to provide a breast pump, which includes a milk bowl; a breast shield detachably connected to the milk bowl, in which a milk storage cavity for storing milk is defined by the breast shield and the milk bowl, and in which the breast shield has a flange shaped to fit a breast and a milk pumping channel for receiving a nipple; a main body detachably connected to the milk bowl, in which an air pump for generating negative pressure is provided inside the main body, the milk bowl is air communicated with the negative pressure generated by the air pump, and the negative pressure generated by the air pump acts on the milk pumping channel to promote lactation; and a membrane configured to prevent the milk from reaching the air pump, in which an inner surface of the milk bowl is provided with a connecting part connected to the membrane, and the membrane, the connecting part, and at least a part of the milk bowl jointly define a recess or a cavity.

In preferred embodiments, the membrane is formed with a groove, and the connecting part is embedded in the groove.

In preferred embodiments, the breast pump further includes a membrane support for installing the membrane.

In preferred embodiments, the membrane support and the connecting part jointly define an air-side groove or cavity.

In preferred embodiments, the connecting part protrudes from the milk bowl.

In preferred embodiments, the connecting part is ring-shaped.

In preferred embodiments, a sealing structure is provided between the connecting part and the membrane to prevent the milk from reaching the air pump.

In preferred embodiments, a rib is provided between the connecting part and the membrane to prevent the milk from reaching the air pump.

In preferred embodiments, an airway connector is disposed in the milk bowl, and one side of the airway connector is connected to the milk pumping channel and another side of the airway connector is connected to a milk pumping side of the membrane.

In preferred embodiments, a positioning structure for positioning the airway connector on the milk bowl is provided between the milk bowl and the airway connector, so as to prevent a detachment between the connecting part and the membrane.

In preferred embodiments, the positioning structure includes a limiting lug and a limiting groove that limit each other.

In preferred embodiments, a one-way valve connected to the airway connector is further disposed in the milk storage cavity, so that the milk flows in one direction to the milk storage cavity from the airway connector.

Another technical solution provided by the present disclosure is to provide a breast pump, which includes a milk bowl; a breast shield detachably connected to the milk bowl, in which a milk storage cavity for storing milk is defined by the breast shield and the milk bowl, and in which the breast shield has a flange shaped to fit a breast and a milk pumping channel for receiving a nipple; a main body detachably connected to the milk bowl, in which an air pump for generating negative pressure is provided inside the main body, the milk bowl is air communicated with the negative pressure generated by the air pump, and the negative pressure generated by the air pump acts on the milk pumping channel to promote lactation; and a membrane configured to prevent the milk from reaching the air pump, in which the milk bowl is provided with a connecting part connected to the membrane, and a rib is provided between the connecting part and the membrane to prevent a detachment between the connecting part and the membrane.

Yet another technical solution provided by the present disclosure is to provide a breast pump, which includes a milk bowl; a breast shield detachably connected to the milk bowl, wherein a milk storage cavity for storing milk is defined by the breast shield and the milk bowl, and in which the breast shield has a flange shaped to fit a breast and a milk pumping channel for receiving a nipple; a main body detachably connected to the milk bowl, in which an air pump for generating negative pressure is provided inside the main body, the milk bowl is air communicated with the negative pressure generated by the air pump, and the negative pressure generated by the air pump acts on the milk pumping channel to promote lactation; a membrane configured to prevent the milk from reaching the air pump; and a membrane support for installing the membrane, in which the membrane support and the connecting part jointly define an air-side groove or cavity; and a positioning structure for positioning an airway connector on the milk bowl is provided between the milk bowl and the airway connector, so as to prevent a detachment between the connecting part and the membrane.

By virtue of the above technical solution, the present disclosure has the beneficial effects as follows. In the present disclosure, the milk bowl is provided with the connecting part connected to the membrane, and the connecting part is embedded in the membrane, so that when the membrane and the milk bowl are assembled, the connecting part is embedded in the membrane, and the membrane can be firmly assembled in the milk bowl, and is not easy to be pushed away from the ventilation place in the air pump by air pressure.

BRIEF DESCRIPTION OF THE DRAWINGS

In order to more clearly illustrate the technical solutions in the embodiments of the present disclosure or the prior art, the following will briefly introduce the drawings that need to be used in the description of the embodiments or the prior art. Obviously, the accompanying drawings in the following description are only some embodiments of the present disclosure. For those skilled in the art, other drawings can also be obtained according to these drawings without any creative effort.

Figure 1:
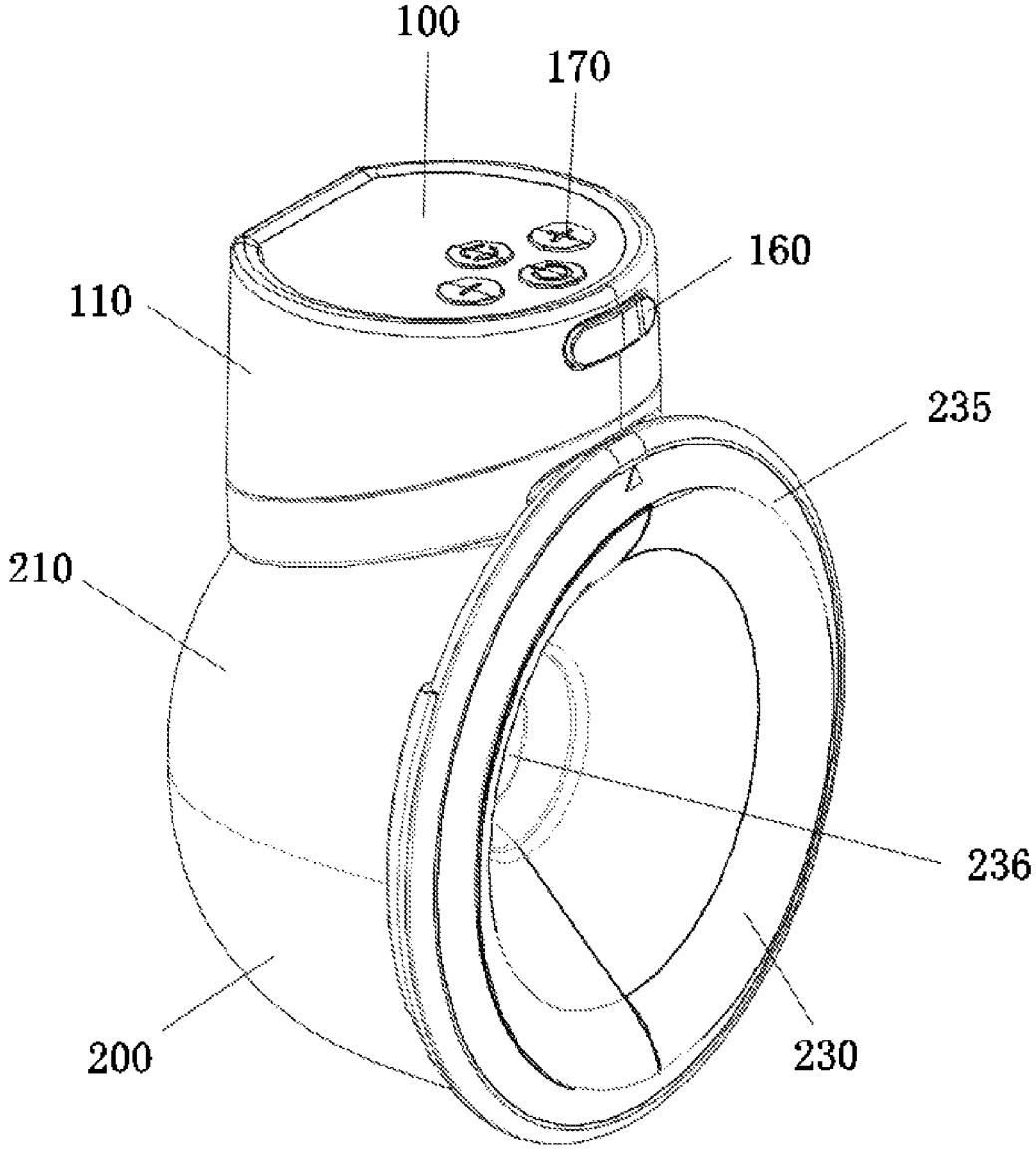
FIG. 1 a schematic structural diagram of a breast pump when a main body and a milk collector are in a combined state.

Reference numeral: 100, main body; 110, housing; 111, connecting groove; 112, elastic protrusion; 113, spring groove; 114, arc-shaped protrusion; 115, charging hole; 116, hole plug; 117, positioning groove; 118, positioning rib; 120, circuit board; 121, charging member; 130, air pump; 140, pressure relief valve; 150, battery; 160, dust plug; 170, button; 171, switch key; 172, mode key; 173, gear increase key; 174, gear reduce key; 180, elastic sealing member; 200, milk collector; 210, milk bowl; 211, connecting post; 212, second groove; 213, arc-shaped groove; 214, placement plane; 215, clamping flange; 216, milk outlet; 217, hole wall; 218, connecting part; 219, limiting groove; 220, milk storage cavity; 230, breast shield; 231, connector; 232, sealing ring; 233, mounting groove; 234, liquid inlet groove; 235, flange; 236, milk pumping channel; 240, airway connector; 241, suction port; 242, milk flowing port; 243, negative pressure port; 244, limiting lug; 245, membrane support; 250, one-way valve; 260, membrane; 261, groove; 262, rib; 300, ventilation tube; a, first surface; b, second surface; c, third surface; d, fourth surface.

DETAILED DESCRIPTION OF THE EXEMPLARY EMBODIMENTS

The present disclosure will be described in further detail below in conjunction with the accompanying drawings.

The specific embodiment is only an explanation of the present disclosure, and is not a limitation of the present invention. Those skilled in the art can make modifications to the embodiment as required after reading the specification, and as long as they are within the rights of the present modifications to the embodiment, all claims are protected by the patent law.

The present embodiment relates to a breast pump, which is used to assist a lactating woman to pump the milk in her breast and store the milk.

Reference is made to FIG. 1, in which the breast pump includes: a milk collector 200 and a main body 100. The main body 100 is detachably connected to the milk collector 200.

Figure 2:
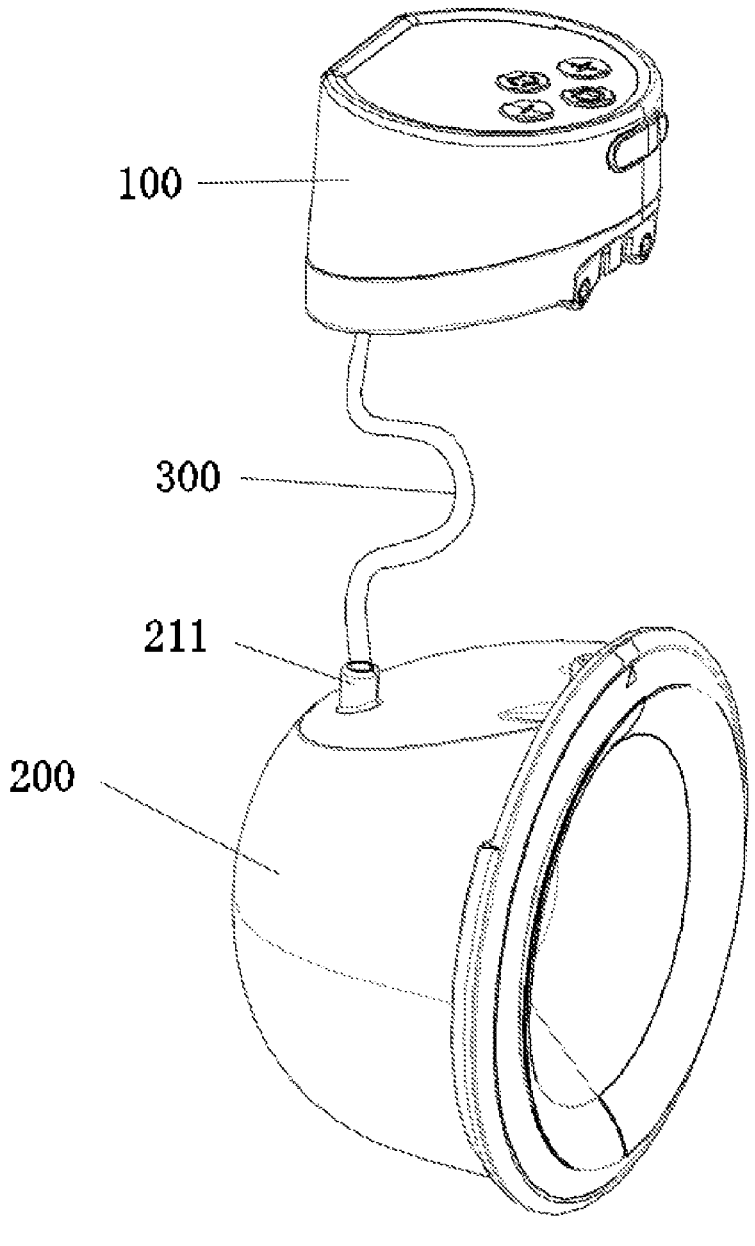
FIG. 2 is a schematic structural diagram of the main body and the milk collector in a detached state, in which they are connected to each other through a ventilation tube.

As a preferred embodiment, as shown in FIG. 2, the breast pump further includes a ventilation tube 300, and two ends of the ventilation tube 30 are detachably and respectively connected to the main body 100 and the milk collector 200.

Figure 3:
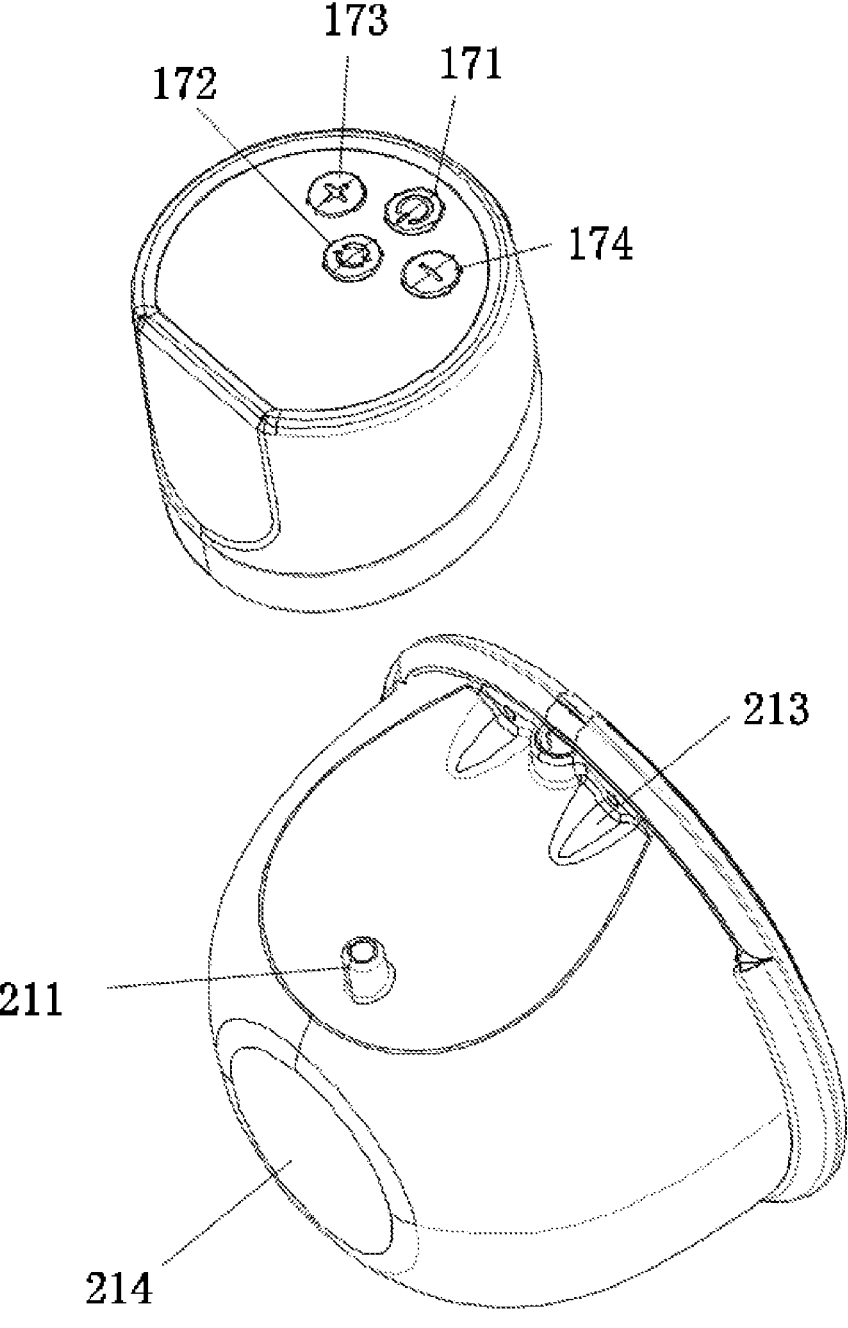
FIG. 3 is a schematic structural diagram of the main body and the milk collector in a detached state.

The breast pump mainly has two usage states, one is a combined state as the breast pump shown in FIG. 1, and the other is a detached state as the breast pump shown in FIG. 2 and FIG. 3. The main body 100 of the breast pump in the combined state is connected to the milk collector 200. After the main body 100 is connected to the milk collector 200, the main body 100 can directly form negative pressure on the milk collector 200, so that the milk collector 200 can pump milk from a breast. When the main body 100 and the milk collector 200 are connected to each other, the breast pump can be directly put into the breastfeeding underwear, which is more convenient to use. The main body 100 of the breast pump in the detached state spatially communicates with the milk collector 200 through the ventilation tube 300. The milk collector 200 is placed on the breast. The main body 100 can be worn on a wearer's waist or head. The main body 100 forms the negative pressure on the milk collector 200 through the ventilation tube 300, so that the milk collector 200 pumps the milk from the breast, and the breast pump in the detached state can avoid a weight of the main body 100 from being loaded on the milk collector 200, thereby avoiding excessive weight on user's breasts. Therefore, a user can selectively switch the breast pump between the detached state and the combined state according to the actual situation. The breast pump has strong compatibility and provides good user experience.

Figure 4:
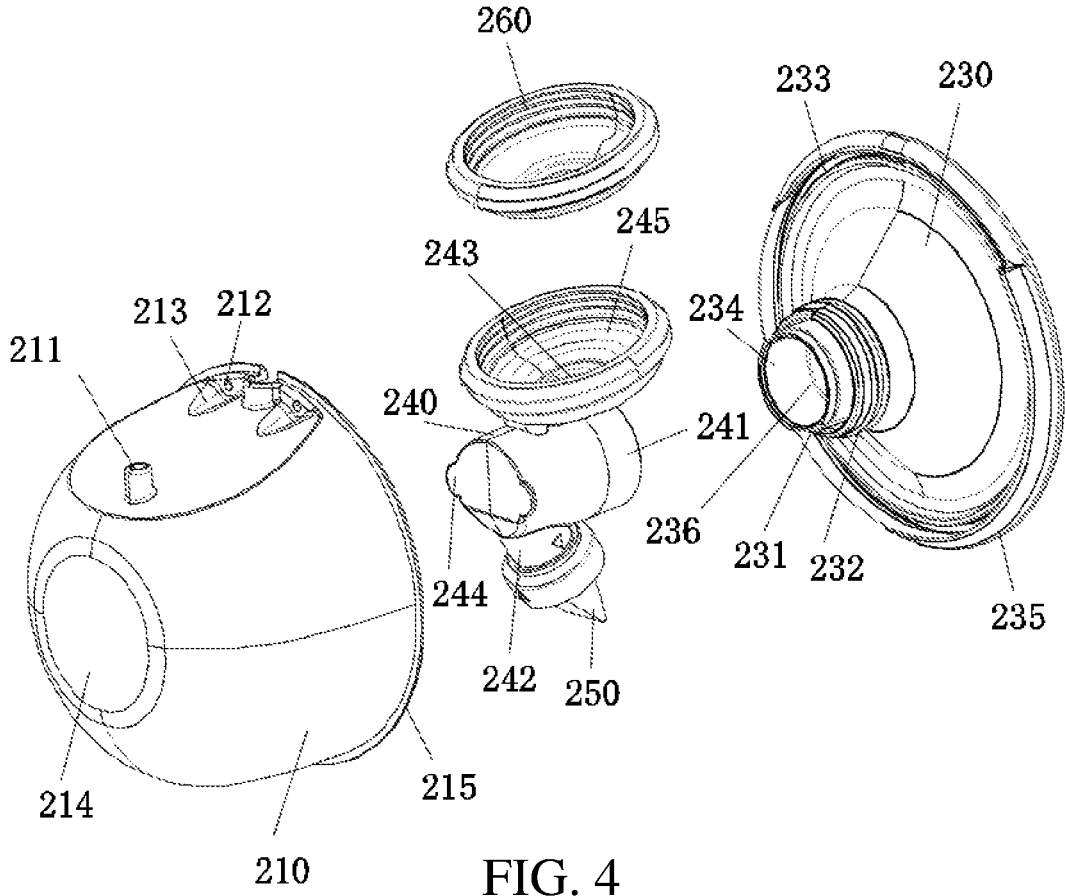
FIG. 4 is a schematic structural exploded diagram of the milk collector.
Figure 7:
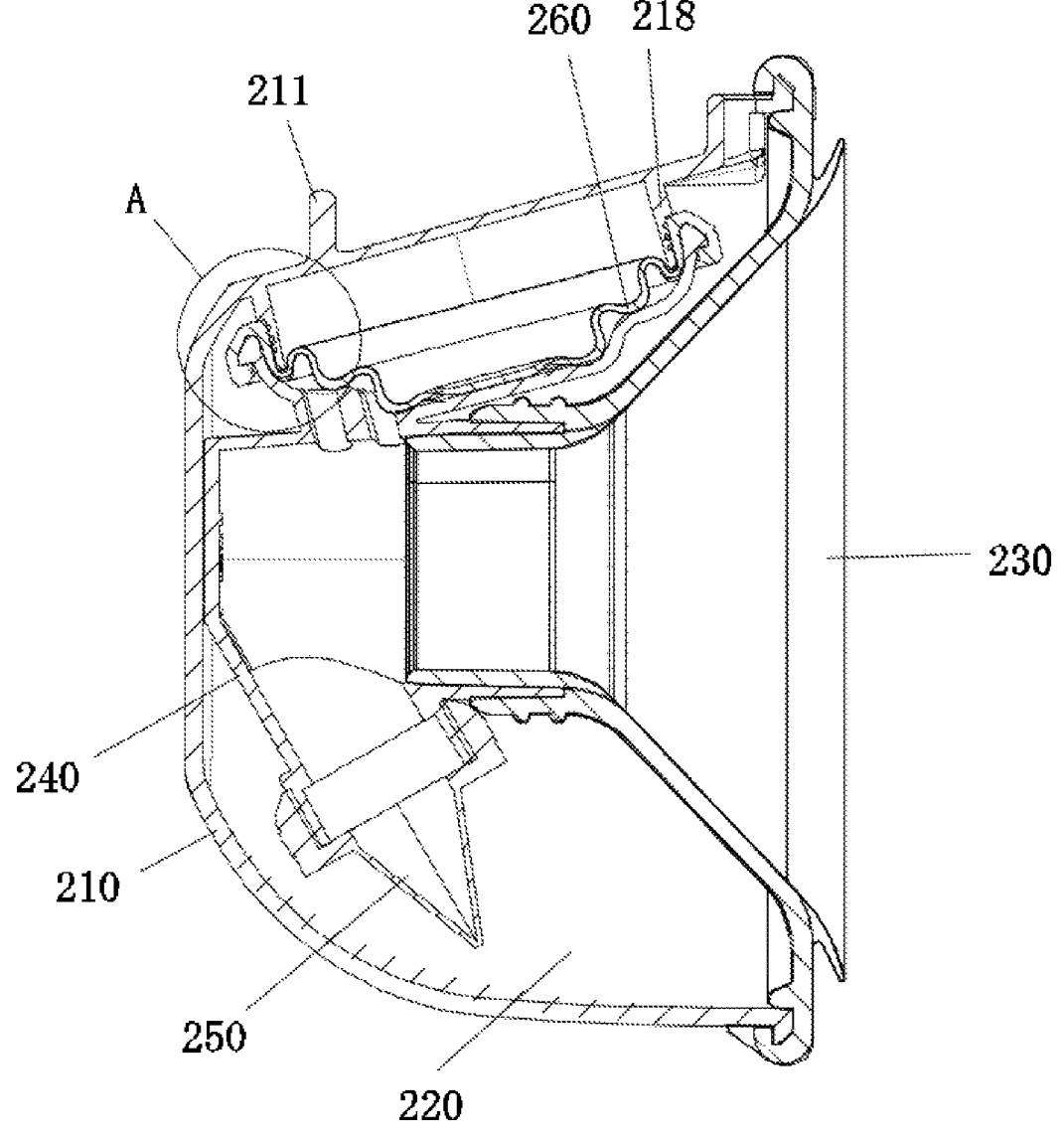
FIG. 7 is a sectional view of the milk collector.

Reference is made to FIG. 4 and FIG. 7, in which the milk collector 200 includes a milk bowl 210, a breast shield 230 detachably connected to the milk bowl 210, such that a milk storage cavity 220 for storing milk is defined by the breast shield 230 and the milk bowl 210, and a membrane 260 that is elastically deformable disposed in the milk storage cavity 220. As shown in FIG. 1 and FIG. 4, the breast shield 230 has a flange 235 shaped to fit the breast and a milk pumping channel 236 for receiving a nipple.

Figure 6:
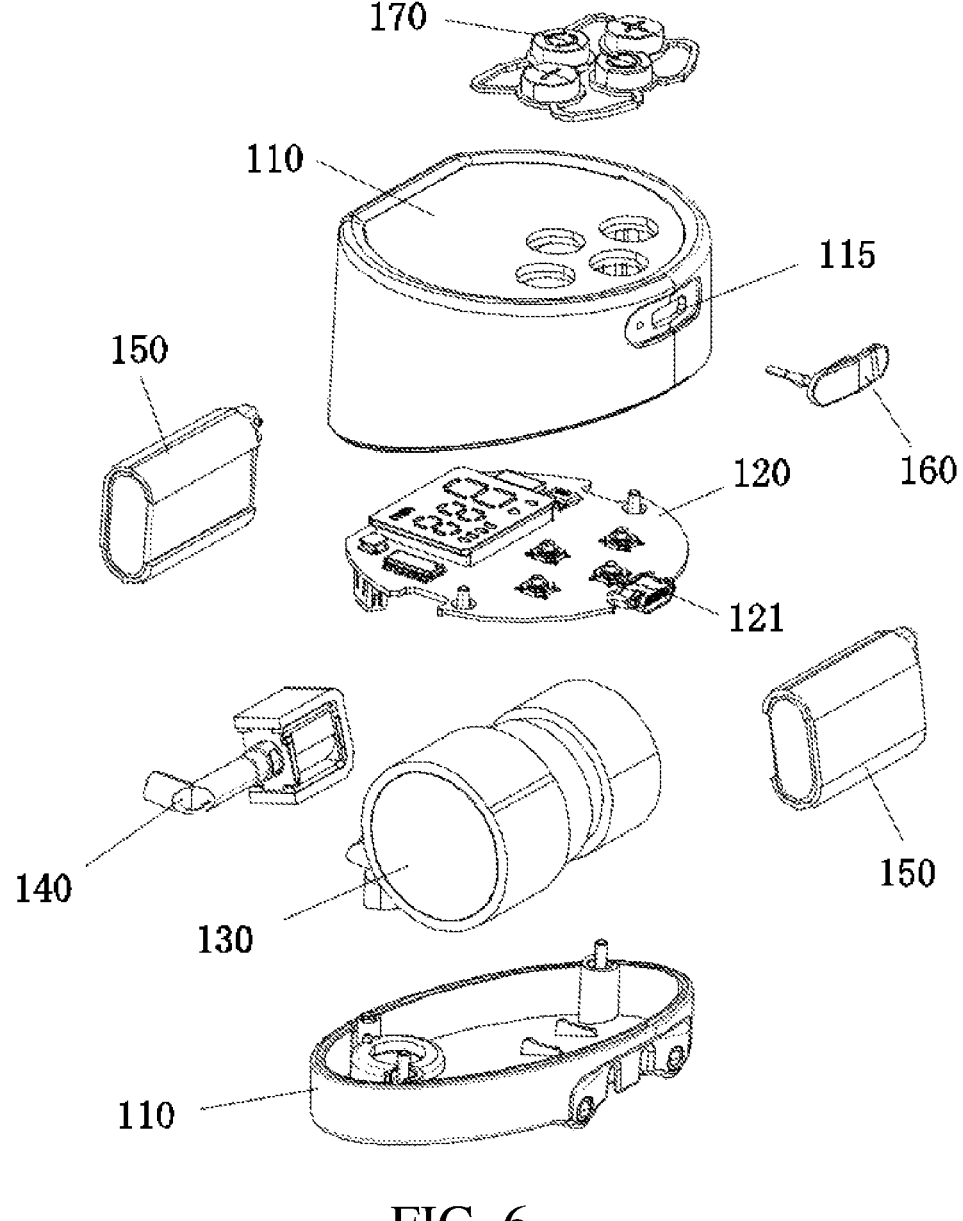
FIG. 6 is a schematic structural exploded diagram of the main body.

Reference is made to FIG. 6, in which the main body 100 includes a housing 110 detachably connected to the milk bowl 210, a circuit board 120 disposed in the housing 110, an air pump 130 for generating the negative pressure on the membrane 260, a pressure relief valve 140 for restoring the air pressure of a space between the membrane 260 and the milk bowl 210, and a battery 150 for supplying power. The milk bowl 210 can air communicate with the negative pressure generated by the air pump 130, and the negative pressure generated by the air pump 130 can act on the milk pumping channel 236 to promote lactation. The membrane 260 is configured to prevent the milk from reaching the air pump 130.

The air pump 130 and the pressure relief valve 140 are spatially communicated with the membrane 260. Specifically, an inlet end of the air pump 130 is in spatial communication with the membrane 260, and an outlet end of the pressure relief valve 140 is in spatial communication with the membrane 260. When working, the air pump 130 draws air, so that a side of the membrane 260 facing away from the air pump generates the negative pressure, which acts on the breast through the negative pressure port 243 and the suction port 241. The breast secretes milk under the action of negative pressure, and the milk in the user's breast flows to the milk storage cavity 220 from the one-way valve 250 through the suction port 241 and the milk flowing port 242. After the air pump 130 stops pumping air, the pressure relief valve 140 takes in air, so that the air pressure on the side of the membrane 260 away from the air pump returns to a normal pressure state.

There are two batteries 150 respectively disposed on two sides of the air pump 130 for powering the negative air pump 130. In the present embodiment, the air pump 130 is a diaphragm pump. In other embodiments, the air pump 130 may also be a piston pump.

Figure 8:
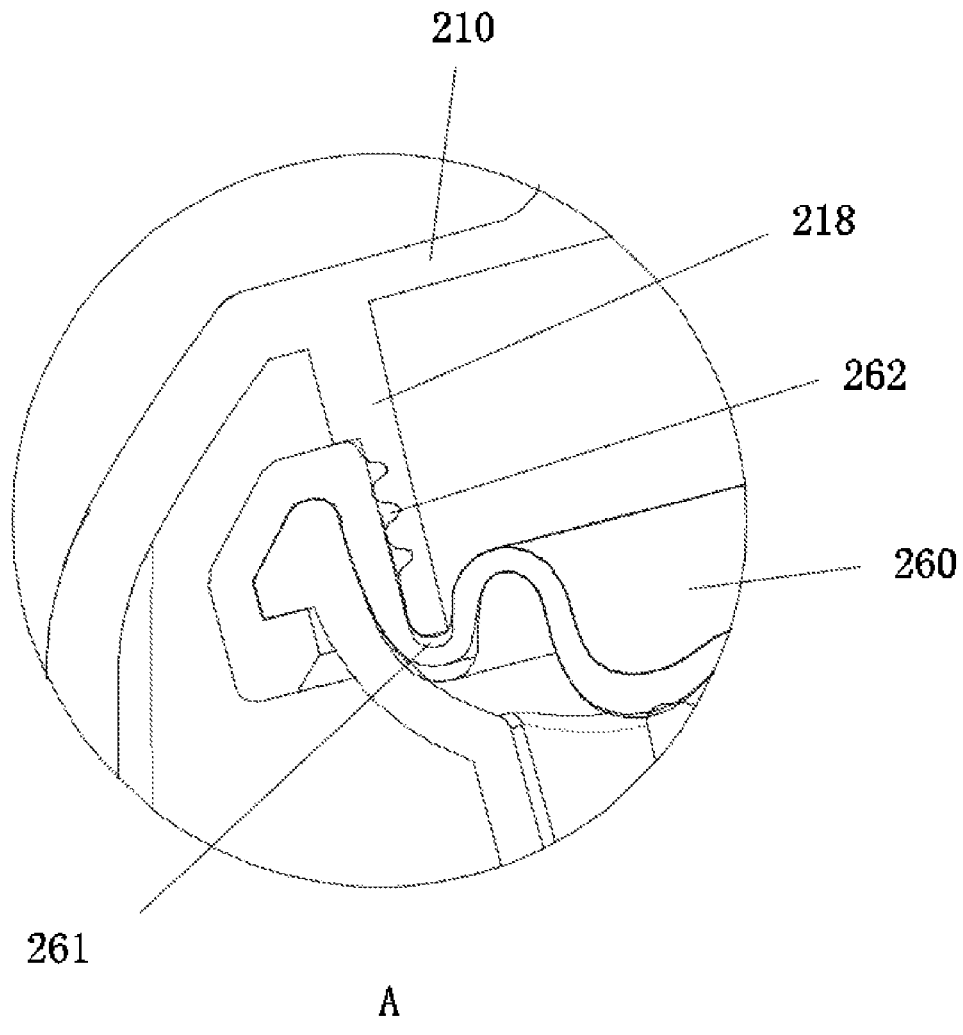
FIG. 8 is an enlarged view of part A in FIG. 7.

In the present embodiment, as shown in FIG. 7 and FIG. 8, the milk bowl 210 is provided with a connecting part 218 connected to the membrane 260, and the connecting part 218 is embedded in the membrane 260, so that when the membrane 260 is assembled with the milk bowl 210, the connecting part 218 is embedded in the membrane 260, and the membrane 260 is firmly assembled in the milk bowl 210, and is not easy to be pushed away from the air pump 130 by the air pressure.

Specifically, in the present embodiment, the membrane 260 is formed with a groove 261, and the connecting part 218 is embedded in the groove 261. More specifically, the connecting part 218 protrudes from the milk bowl 210, and the connecting part 218 is in a ring shape. When the membrane 260 is assembled with the milk bowl 210, the connecting part 218 that is protruding and annular is engaged to the groove 261 of the membrane 260, so that the membrane 260 is firmly assembled in the milk bowl 210.

In order to prevent the milk from reaching the air pump 130, and to ensure a tighter assembly between the connecting part 218 and the membrane 260, a sealing structure is provided between the connecting part 218 and the membrane 260. Specifically, in the present embodiment, as shown in FIG. 8, the sealing structure is a rib 262 provided on the membrane 260. In other embodiments, the sealing structure can also be the rib and a sealing groove arranged between the connecting part 218 and the membrane 260 that are cooperating with each other. In other embodiments, other forms of sealing structures may also be provided.

As a preferred embodiment, as shown in FIG. 4 and FIG. 7, the milk bowl 210 is provided with an airway connector 240. One side of the airway connector 240 is connected to the milk pumping channel 236 and another side of the airway connector 240 is connected to a milk pumping side of the membrane 260. Further, a one-way valve 250 connected to the airway connector 240 is further provided in the milk storage cavity 220, so that the milk flows in one direction to the milk storage cavity 220 from the airway connector 240.

Specifically, in the present embodiment, the airway connector 240 includes a suction port 241, a milk flowing port 242 and a negative pressure port 243 that are in communication with each other. The one side of the airway connector 240 connected to the milk pumping channel 236 is provided with the suction port 241, the another side of the airway connector 240 connected to the milk pumping side of the membrane 260 is provided with the negative pressure port 243, the airway connector 240 is connected to the one-way valve 250, and still another side of the airway connector 240 connected to the one-way valve 250 is provided with the negative pressure port 243. That is, the milk pumping port 241 is connected to the breast shield 230, the milk flowing port 242 is connected to the one-way valve 250, and the negative pressure port 243 is connected to the membrane 260.

As a preferred embodiment, as shown in FIG. 4, the breast pump is further provided with a membrane support 245 for mounting the membrane 260. The membrane support 245 and the connecting part 218 jointly define an air-side groove or cavity. Specifically, in the present embodiment, the membrane support 245 is integrally formed with the airway connector 240, and the membrane support 245 spatially communicates with the negative pressure port 243.

Figure 5:
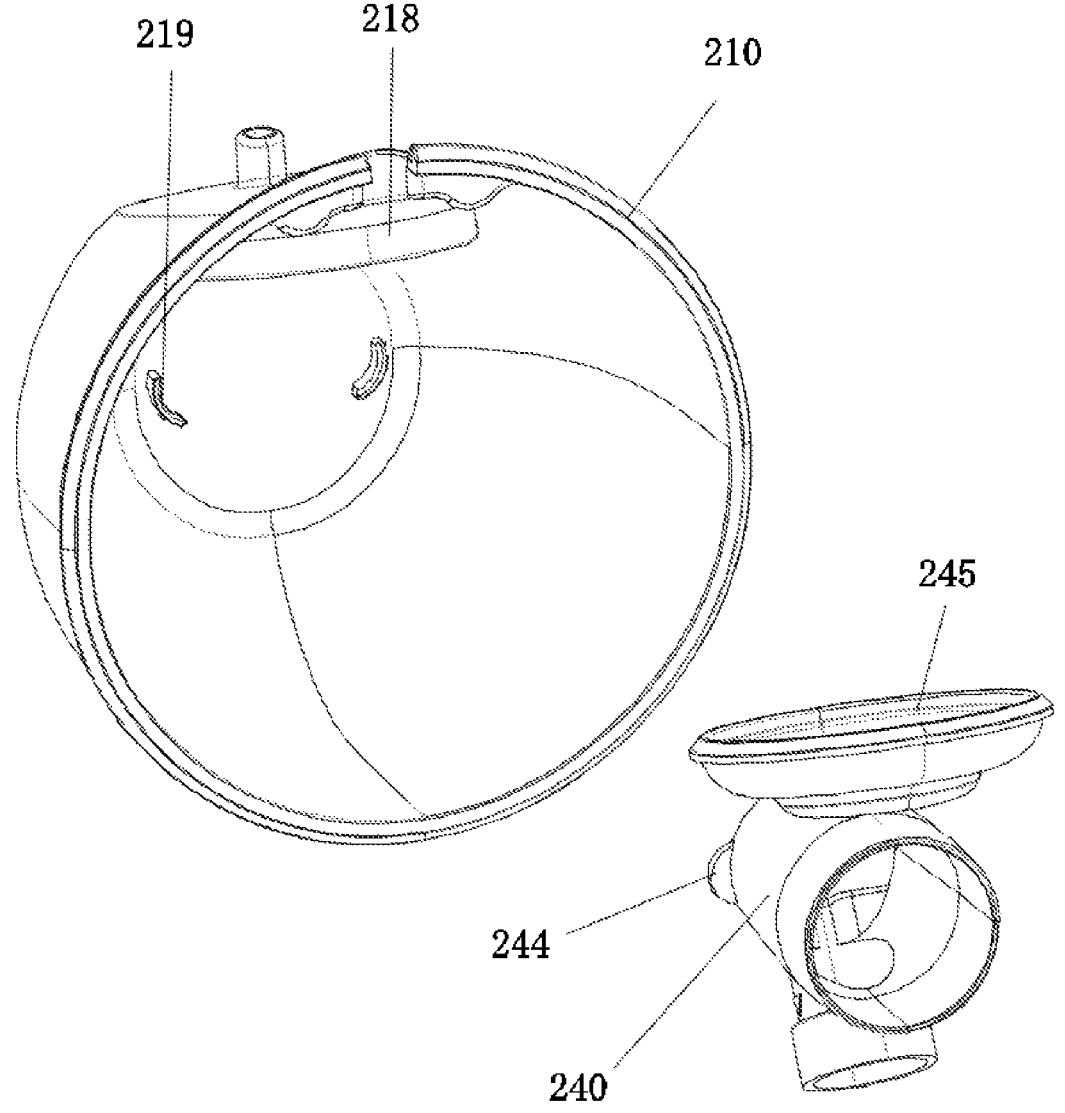
FIG. 5 is a schematic structural diagram of a milk bowl and an airway connector.

In order to further restrict the connecting part 218 and the membrane 260 from being detached from each other, a positioning structure for positioning the airway connector 240 on the milk bowl 210 is provided between the milk bowl 210 and the airway connector 240. As a preferred embodiment, as shown in FIG. 5, the positioning structure includes a limiting lug 244 and a limiting groove 219 that limit each other. Specifically, in the present embodiment, the limiting lug 244 is arranged on the airway connector 240, and the limiting groove 219 is arranged on an inner wall of the milk bowl 210. During installation, when the airway connector 240 is installed into the milk bowl 210, the limiting lug 244 is engaged to the limiting groove 219. More specifically, there are two limiting lugs 244, outer walls of the two limiting lugs 244 are arc-shaped, and the two limiting lugs 244 are symmetrically arranged on the airway connector 240. There are also two limiting grooves 219, and inner walls of the two limiting grooves 219 are correspondingly arc-shaped. The limiting groove 219 cooperates with the limiting lug 244. In addition to supporting the airway connector 240, the limiting lug 244 and the limiting groove 219 can further limit a movement of the airway connector 240. The limiting groove 219 is installed on an inner surface of the milk bowl 210 opposite to the breast shield 230.

Figure 12:
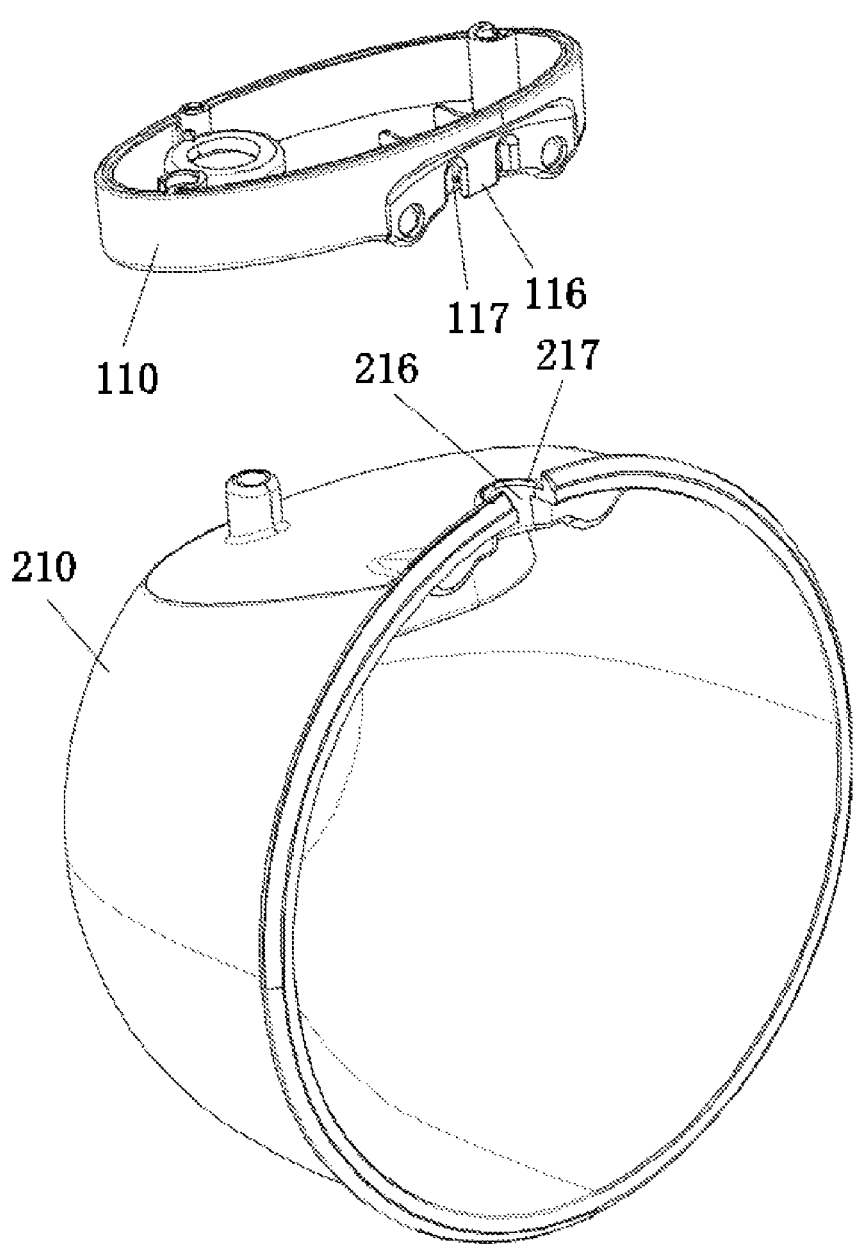
FIG. 12 is a schematic structural diagram of another perspective of the housing and the milk bowl.

In the present embodiment, as shown in FIG. 12, the milk bowl 210 is provided with a milk outlet 216 spatially communicating with the milk storage cavity 220, and the housing 110 is provided with a hole plug 116 which can be engaged to the milk outlet 216 when it is assembled with the milk bowl 210, and is used for partially sealing the milk outlet 216. When the milk bowl 210 is configured to attach to the breast, the milk outlet 216 faces upward. By setting the hole plug 116 on the housing 110, when the milk bowl 210 is assembled with the main body 100, the hole plug 116 partially seals the milk outlet 216 of the milk bowl 210, which helps to prevent external foreign matter from falling into the milk storage cavity 220 through the milk outlet 216, and ensures that the milk is not polluted. In addition, it also helps to prevent the milk in the milk storage cavity 220 from spilling out when the user shakes it. When the milk bowl 210 is configured to attach to the breast, the setting of the milk outlet 216 facing upward makes the milk not overflow from the milk outlet 216 when the breast pump is working.

In the present embodiment, the hole plug 116 partially seals the milk outlet 216 of the milk bowl 210, leaving a ventilation channel through which the outside air communicates with the milk storage cavity 220, so as not to affect the flow of milk into the milk storage cavity 220. In some embodiments, the hole plug 116 can be configured to fully seal the milk outlet 216, but it is necessary to provide the ventilation channel at other positions of the milk bowl 210 to spatially communicate the milk storage cavity 220 with the outside air.

In the present embodiment, as shown in FIG. 12, the milk outlet 216 is arranged on an outer edge of the milk bowl 210. The milk outlet 216 has an arc-shaped inner wall surface, and the hole plug 116 has an arc-shaped outer wall surface corresponding to the milk outlet 216. The milk outlet 216 is arranged on the outer edge of the milk bowl 210 and has an arc-shaped inner wall, so that the user can pour out the milk stored in the milk storage cavity 220 along the arc-shaped inner wall of the milk outlet 216.

More specifically, the milk outlet 216 is semi-cylindrical shaped, and the hole plug 116 is also semi-cylindrical shaped.

When the housing 110 is assembled with the milk bowl 210, the outer wall of the hole plug 116 is spaced apart from the inner wall of the milk outlet 216, so as to leave the ventilation channel through which the outside air is in air communication with the milk storage cavity 220.

In the present embodiment, as shown in FIG. 12, the housing 110 is provided with a positioning groove 117, the hole plug 116 extends from a groove bottom of the positioning groove 17, and the milk bowl 210 is provided with a hole wall 217 defining the milk outlet 216. When the housing 110 is assembled with the milk bowl 210, the hole plug 116 is engaged to the milk outlet 216, and the hole wall 217 is engaged to the positioning groove 117, so that a cooperation between the hole plug 116 and the milk outlet 216 is more stable.

In a preferred embodiment, a sidewall of the positioning groove 117 is arc-shaped, and an outer wall of the hole wall 217 has an arc-shaped outer wall corresponding to the sidewall of the positioning groove 117.

In a preferred embodiment, the positioning groove 117 is semi-cylindrical shaped, and the hole wall 217 is semi-cylindrical shaped corresponding to the side wall of the positioning groove 117.

Figure 13:
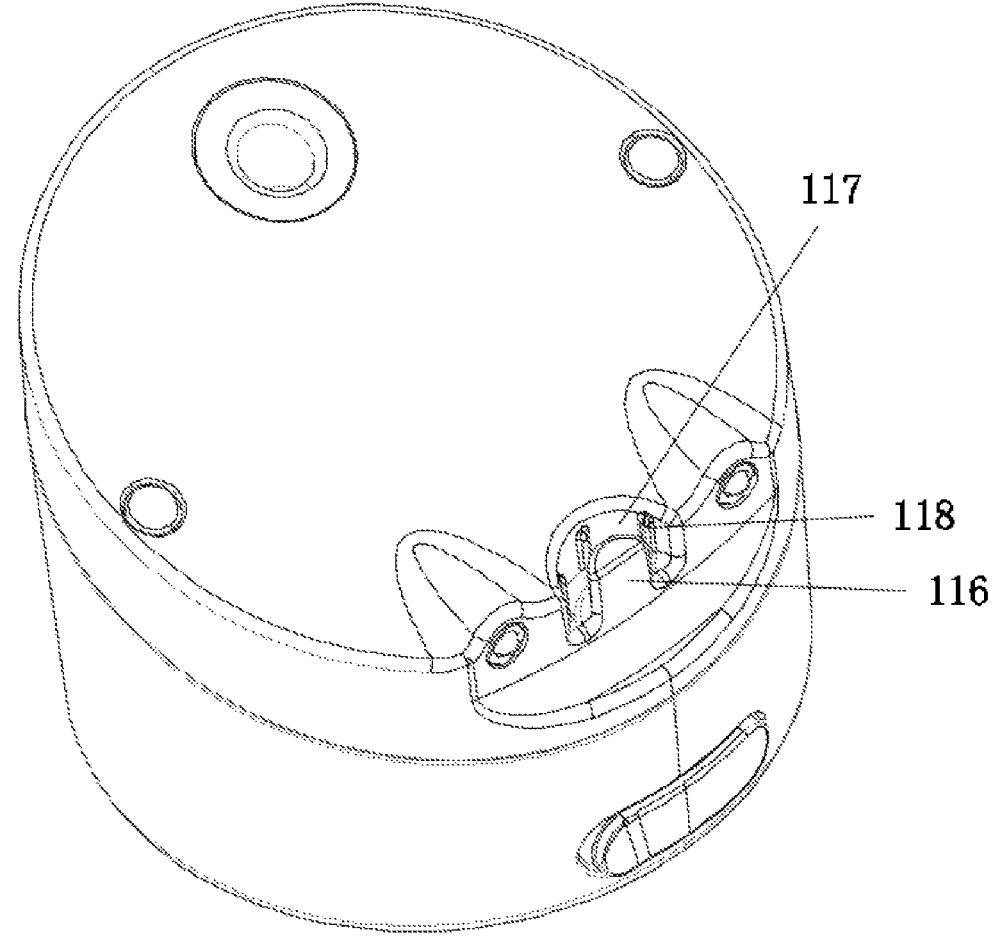
FIG. 13 is a schematic structural diagram of the main body.

As shown in FIG. 13, the side wall of the positioning groove 117 is provided with a positioning rib 118, so that when the hole plug 116 is engaged to the milk outlet 216, the positioning rib 118 abuts against the outer wall surface of the hole wall 217, and the assembly of the hole plug 116 and the milk outlet 216 becomes tighter. In the present embodiment, there are three positioning ribs 118, which are distributed on the sidewall of the positioning groove 117 with equal arcs. In other embodiments, other numbers of positioning ribs 118 can be provided, preferably two or more.

Figure 9:
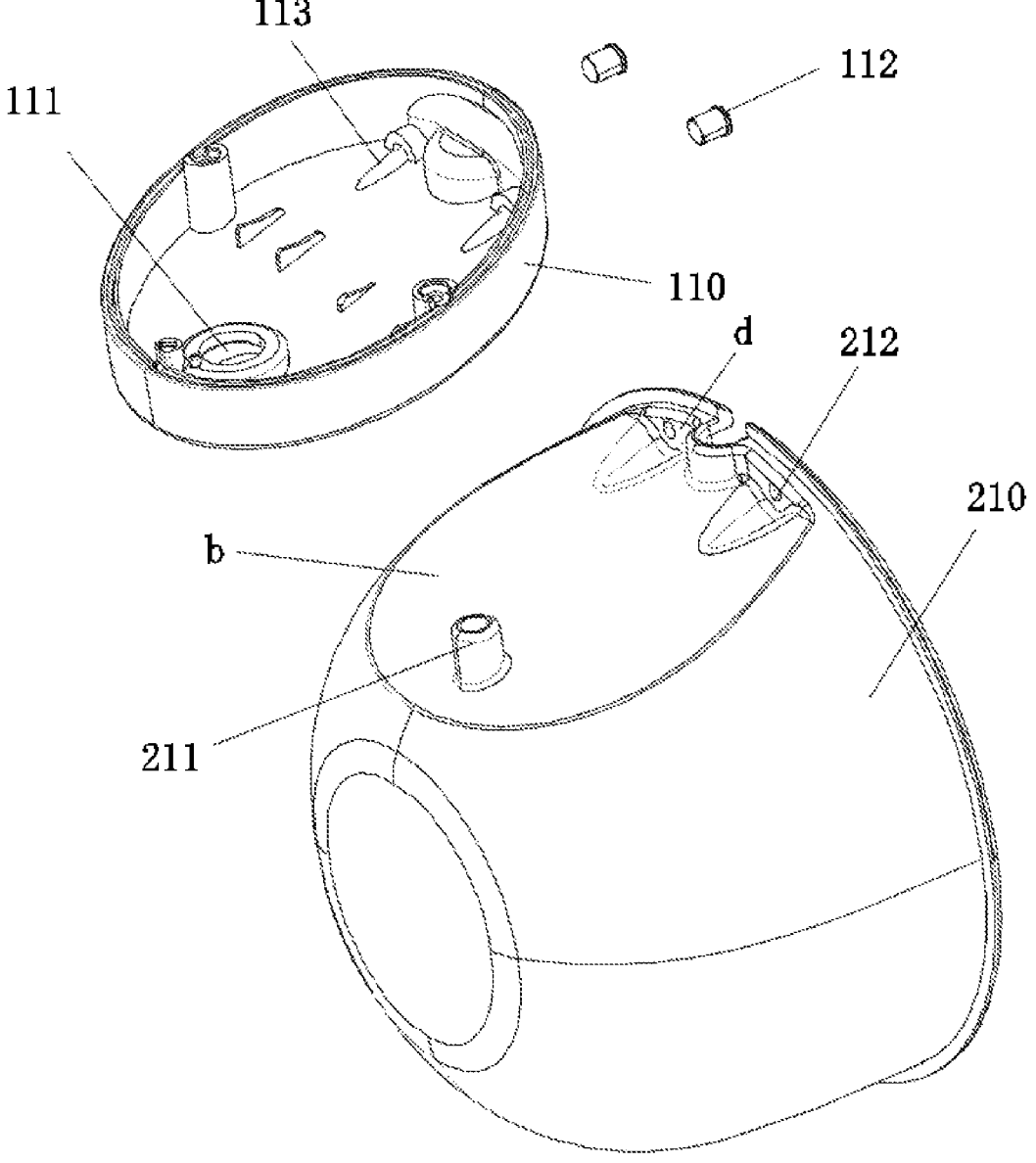
FIG. 9 is a schematic structural diagram of a housing and the milk bowl.
Figure 10:
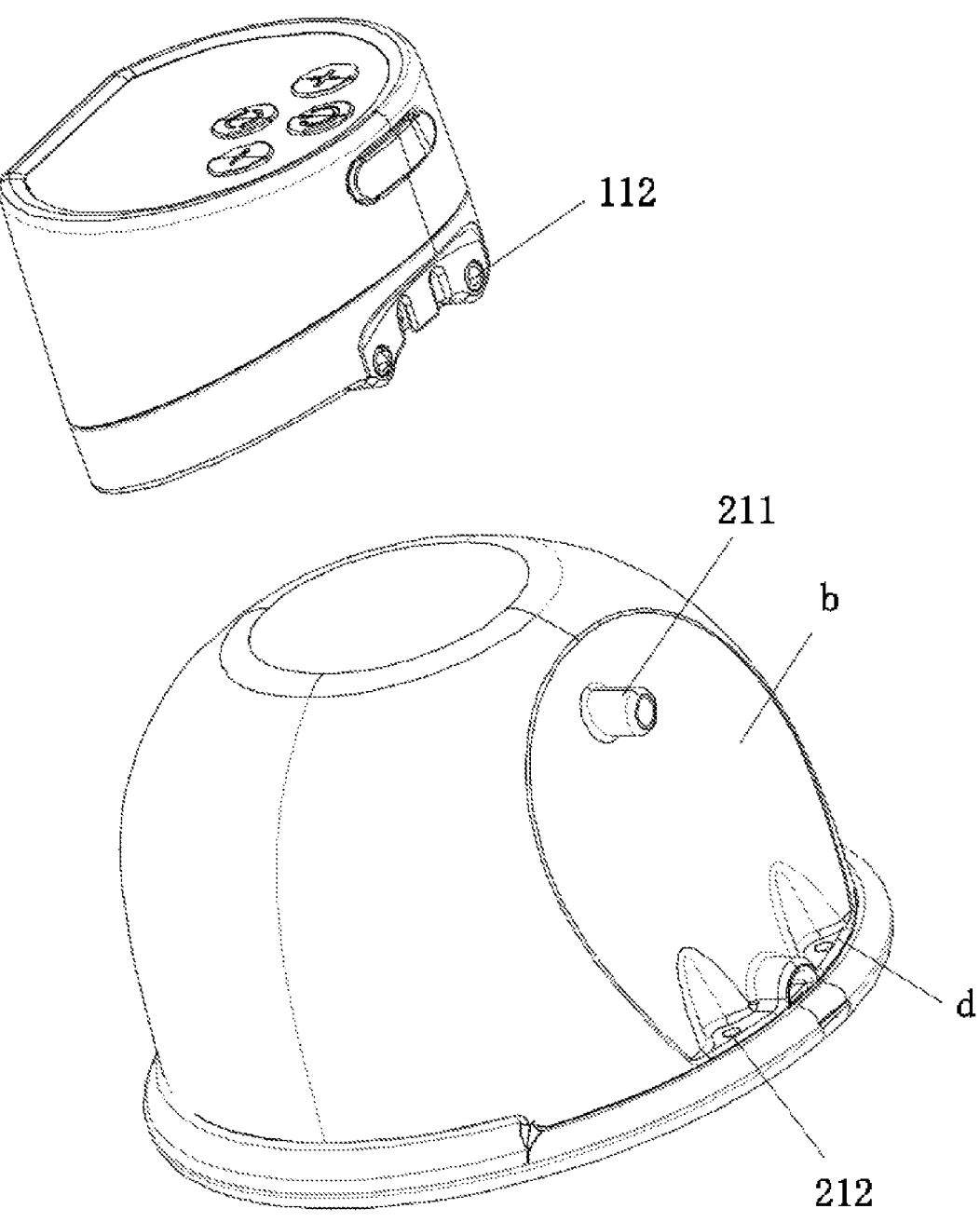
FIG. 10 is a schematic structural diagram of one perspective view of the main body and the milk collector.

In the present embodiment, as shown in FIG. 9 and FIG. 10, the milk bowl 210 is provided with a connecting post 211, the housing 110 is provided with a connecting groove 111, and the connecting post 211 is detachably engaged to the connecting groove 111. The housing 110 is provided with an elastic protrusion 112, and the milk bowl 210 is provided with a second groove 212 corresponding to the elastic protrusion 112. An included angle is formed between the engagement direction of the connecting post 211 relative to the connection groove 111 and the engagement direction of the elastic protrusion 112 relative to the second groove 212. When the housing 110 is assembled with the milk bowl 210, the connecting post 211 is fittingly engaged to the connecting groove 111 to spatially communicate the membrane 260 with the air pump 130. In addition, the elastic protrusion 112 is placed in the second groove 212, and the engagement of the connecting post 211 relative to the connecting groove 111 combined with the engagement of the elastic protrusion 112 relative to the second groove 212 makes the assembly between the milk bowl 210 and the main body 100 very stable, and the milk bowl 210 is not easy to detach relative to the main body 100. Further, when the milk bowl 210 is assembled with the main body 100, a cooperation between the elastic protrusion 112 and the second groove 212 will make a specific sound, such as "click", to give feedback to the user and let the user know that it has been assembled properly.

More specifically, the included angel between the engagement direction of the connecting post 211 relative to the connecting groove 111 and the engagement direction of the elastic protrusion 112 relative to the second groove 212 is 90 degrees, so that when assembled, the connecting post 211 and the connecting groove 111 provide a guiding function to the assembly of the main body 100 and the milk collector 200. The main body 100 and the milk collector 200 can be assembled along the engagement direction of the connecting post 211 relative to the connecting groove 111, and the main body 100 and the milk collector 200 are limited to detach along the engagement direction of the connecting post 211 and the connecting groove 111. Similarly, the elastic protrusion 112 and the second groove 212 limit the detachment of the main body 100 and the milk collector 200 at different positions in the same direction.

In other embodiments, the connecting post 211 and the connecting groove 111 are installed on different planes from the elastic protrusion 112 and the second groove 212, and the two installation planes are arranged at an included angle.

In other embodiments, the housing 110 may also be provided with the connecting post 211, and the milk bowl 210 may be provided with the connecting groove 111. The milk bowl 210 may also be provided with the elastic protrusion 112, and the housing 110 may be provided with the second groove 212 corresponding to the elastic protrusion. 112. In addition, the included angel between the engagement direction of the connecting post 211 relative to the connection groove 111 and the engagement direction of the elastic protrusion 112 relative to the second groove 212 can also be 45 degrees, 60 degrees, 70 degrees, 75 degrees, 80 degrees, 85 degrees, etc.

Figure 11:
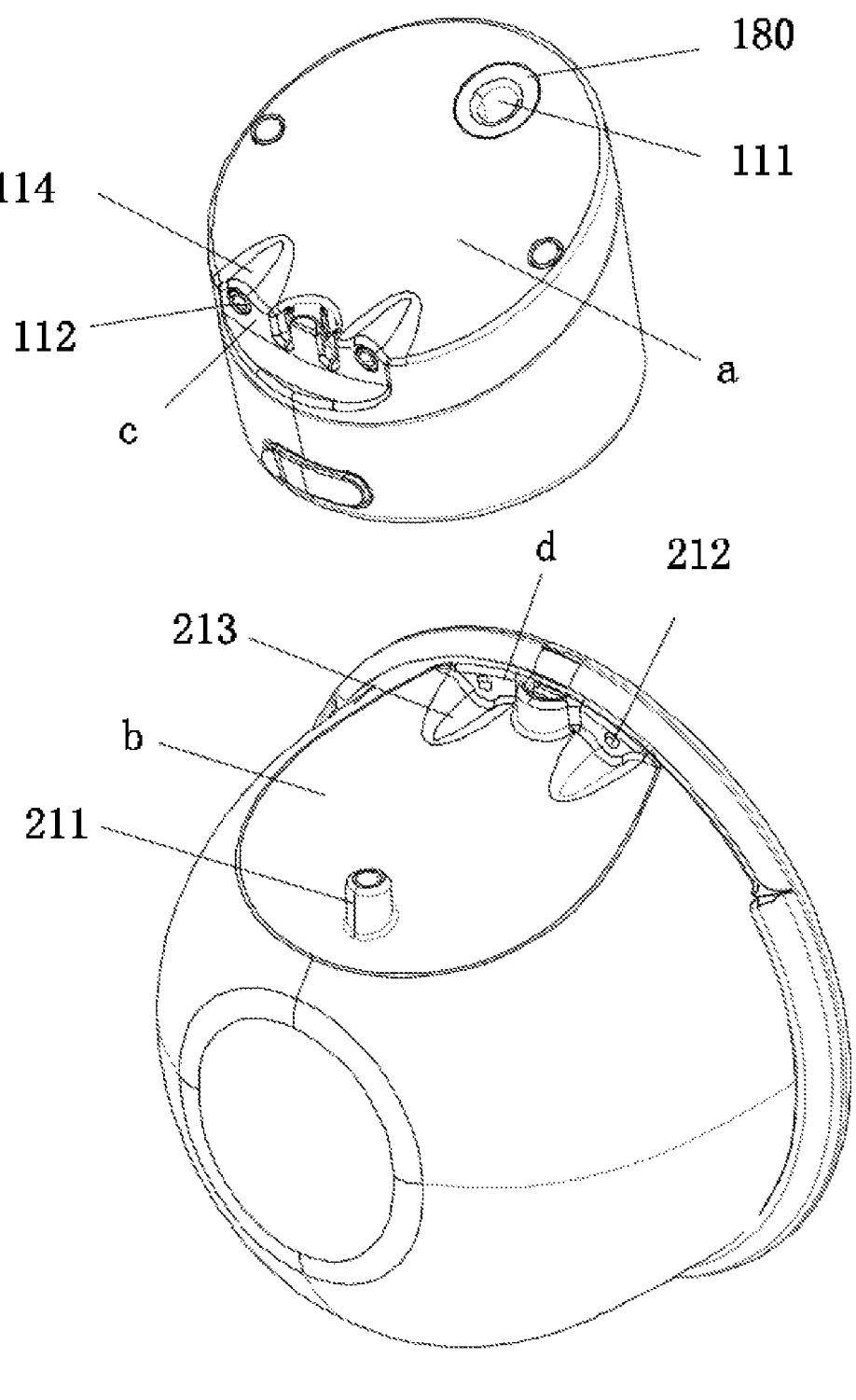
FIG. 11 is a schematic structural diagram of another perspective of the main body and the milk collector.

As a preferred embodiment, as shown in FIG. 11, an elastic sealing member 180 is provided on the groove wall surface of the connecting groove 111. By providing the elastic sealing member 180, the seal and the tightness are improved after the connecting post 211 is engaged to the connection groove 111.

In the present embodiment, there are two elastic protrusions 112 and two second grooves 212. In this way, the connecting post 211 and the connecting groove 111 form a fixed point, and each pair of the elastic protrusions 112 and the second grooves 212 form a fixed point. In this way, the assembly between the milk bowl 210 and the main body 100 is more stable through the three-point limit. In the three connecting and assembling points, the connecting and assembling points of the connecting post 211 and the connecting groove 111 are not in the same plane as the other two connecting and assembling points, and the two pairs of the elastic protrusions 112 and the two pairs of the second grooves 212 can form a limit in the same direction as the engagement direction of the connecting post 211 relative to the connecting groove 111 to the milk bowl 210 and the main body 100, and also form a limit the connecting direction between the two pairs of the elastic protrusions 112 and the second groove 212, and can further limit the milk bowl 210 moving along the engagement direction of the elastic protrusion 112 and the second groove 212 relative to the housing 110, and can restrict the milk bowl 210 from detaching from the housing 110 along the direction. Preferably, the connecting post 211 and the connecting groove 111 are located on a center line of a connecting direction between the two pairs of elastic protrusions 112 and the second grooves 212. In some embodiments, other numbers of elastic protrusions 112 and second grooves 212 may also be provided.

For ease of understanding, as shown in FIG. 10 and FIG. 11, a surface where the connecting post 211 and the connecting groove 111 are located is defined as a first contact surface between the housing 110 and the milk bowl 210, and the surface where the elastic protrusion 112 and the second groove 212 are located is defined as a second contact surface between the housing 110 and the milk bowl 210. Specifically, in the present embodiment, one surface of the first contact surface at the housing 110 is defined as the first surface a, and another surface of the first contact surface at the milk bowl 210 is defined as a second surface b. One surface of the second contact surface at the housing 110 is defined as a third surface c, and another surface of the second contact surface at the milk bowl 210 is defined as a fourth surface d.

In the present embodiment, in order to further improve the assembly stability between the milk bowl 210 and the main body 100, the connecting post 211 is located on an end of the second surface b away from the fourth contact surface d, and the connecting groove 111 is correspondingly located on an end of the first surface a away from the third surface c.

As shown in FIG. 9, the housing 110 is provided with a spring groove 113, and the elastic protrusion 112 includes a protruding piece whose head can extend out of the spring groove 113 and whose tail is restricted in the spring groove 113, and a spring (not shown) disposed in the spring groove 113, of which one end abuts against the protrusion, and of which another end abuts against the inner wall of the spring groove 113. The head of the protruding piece is spherical, and the second groove 212 is a spherical groove 212 adapted thereto.

When the housing 110 is assembled with the milk bowl 210, the head of the elastic protrusion 112 is pressed by the outer wall of the second contact surface of the milk bowl 210, at this time the elastic protrusion 112 retracts into the spring groove 113, and the spring is under compression state. When the housing 110 moves to the position where the elastic protrusion 112 is aligned with the second groove 212, since the head of the elastic protrusion 112 is no longer pressed by the outer wall of the second contact surface of the milk bowl 210, the returned spring pushes out the elastic protrusion 112, at this time the head of the elastic protrusion 112 pushes into the second groove 212 of the milk bowl 210, and the cooperation between the elastic protrusion 112 and the second groove 212 will make a specific sound, thereby providing feedback to the user and letting the user know it has been assembled properly.

In other embodiments, the elastic protrusion 112 and the second groove 212 can also be arranged at other positions, and the specific structure can also be modified, as long as the elastic protrusion 112 can stretch in and out of the second groove 212.

Further, as shown in FIG. 11, the outer wall of the spring groove 113 is formed with an arc-shaped protrusion 114 on the first contact surface, and the milk bowl 210 is formed with a corresponding arc-shaped groove 213 on the first contact surface. The arc-shaped protrusion 114 and the arc-shaped groove 213 can guide the assembly of the milk bowl 210 and the housing 110.

As shown in FIG. 6, in the present embodiment, the housing 110 is provided with a charging hole 115, and the charging member 121 on the circuit board 120 is connected to an external power source through the charging hole 115 so as to charge the battery 150.

A dust plug 160 is provided at the charging hole 115, and the dust plug 160 is used to plug into the charging hole 115. When not charging, the dust plug 160 can be engaged with the charging hole 115 to prevent the charging hole 115 from dust and avoid affecting subsequent charging.

Referring to FIG. 3 and FIG. 6, a plurality of buttons 170 correspondingly connected to the circuit board 120 are provided on an upper side of the housing 110, comprising a switch key 171, a mode key 172, a gear increase key 173 and a gear reduce key 174. Pressing and holding the on/off key 171 circularly can control the power on or off of the circuit board 120 to enter the power-on mode or the power-off mode. In the power-on mode, pressing the mode key 172 cyclically can switch pausing/starting the air pump 130 cyclically. In the power-on mode, pressing the gear increase key 173 can control the air pressure of the air pump 130 to increase, so that the vacuuming intensity and pressurization intensity of the air pump 130 become greater. In the power-on mode, pressing the gear down key 174 can control the air pressure of the air pump 130 to decrease, so that the vacuuming intensity and pressurization intensity of the air pump 130 decrease.

In the present embodiment, the color of the milk bowl 210 is transparent, and the outer wall of the milk bowl 210 is provided with a capacity scale (not shown), which is convenient for observing the milk capacity contained in the milk storage cavity 220 in the milk bowl 210, and reminds the user whether to continue pumping milk.

Referring to FIG. 3, the side of the milk bowl 210 facing away from the breast shield 230 has a placement plane 214, and the placement plane 214 is planar, so that the milk bowl 210 can be placed on the desktop through the placement plane 214.

Referring to FIG. 4, the breast shield 230 is funnel-shaped, the side of the breast shield 230 facing the milk bowl 210 has a connector 231, and the connector 231 is used for detachably engaged to the suction port 241 of the airway connector 240. A sealing ring 232 is sleeved on the connector 231, and the sealing ring 232 is used to seal the gap between the connector t 231 and the airway connector 240, so as to ensure the tightness of the connection between breast shield 230 and the airway connector 240.

The breast shield 230 is provided with an annular mounting groove 233 facing a circumferential edge of the milk bowl 210, and the mounting groove 233 is detachably engaged to the engagement flange 218 of the milk bowl 210. It can be understood that, in other embodiments, the breast shield 230 and the milk bowl 210 may also be connected to each other in other detachable ways, such as magnetic connection, screw connection, etc., which are not limited herein. When the milk in the milk storage cavity 220 needs to be poured out, the breast shield 230 can be disassembled and detached from the milk bowl 210. When pumping milk is needed, the breast shield 230 can be connected with the milk bowl 210.

The breast shield 230 has a liquid inlet groove 234 that is hollow. When the liquid inlet groove 234 is connected to a milk inlet of the airway connector 240, an end of the breast shield 230 facing away from the milk bowl 210 is configured to attach to the breast. When the airway connector 240 is evacuated, the liquid inlet groove 234 forms a negative pressure to pump the milk in the mammary gland. The milk flows to the milk inlet of the airway connector 240 through the liquid inlet groove 234, and then flows to the milk storage cavity 220 in the milk bowl 210 through the one-way valve 250. Specifically, in the present embodiment, the one-way valve 250 is a duckbill valve.

The above is only used to illustrate the technical solution of the present disclosure and not to limit it. Other modifications or equivalent replacements made by those skilled in the art to the technical solution of the present disclosure, as long as they do not deviate from the spirit and scope of the technical solution of the present invention, shall be covered by the claims of the present disclosure.

What is claimed is:

1. A breast pump, comprising:
a milk bowl,
a breast shield detachably connected to the milk bowl, wherein a milk storage cavity for storing milk is defined by the breast shield and the milk bowl, and the breast shield has a flange shaped to fit a breast and a milk pumping channel for receiving a nipple;
a main body detachably connected to the milk bowl, wherein an air pump for generating negative pressure is provided inside the main body, the milk bowl is air communicated with the negative pressure generated by the air pump, and the negative pressure generated by the air pump acts on the milk pumping channel to promote lactation;
a membrane configured to prevent the milk from reaching the air pump, wherein an inner surface of the milk bowl is provided with a connecting part connected to the membrane, and the membrane, the connecting part, and at least a part of the milk bowl jointly define a recess or a cavity; and
an airway connector disposed in the milk bowl, wherein one side of the airway connector is connected to the milk pumping channel and another side of the airway connector is connected to a milk pumping side of the membrane, and a positioning structure for positioning the airway connector on the milk bowl is provided between the milk bowl and the airway connector, so as to prevent a detachment between the connecting part and the membrane.

2. The breast pump according to claim 1, wherein the membrane is formed with a groove, and the connecting part is embedded in the groove.

3. The breast pump according to claim 1, further comprising a membrane support for installing the membrane.

4. The breast pump according to claim 3, wherein the membrane support and the connecting part jointly define an air-side groove or cavity.

5. The breast pump according to claim 1, wherein the cavity jointly defined by the membrane, the connecting part and the at least a part of the inner surface of the milk bowl is an air-side negative pressure cavity.

6. The breast pump according to claim 1, wherein the milk bowl is provided with a connecting post for conducting the negative pressure to the membrane.

7. The breast pump according to claim 1, wherein the milk bowl is provided with a connecting post for being engaged to an inside of the main body.

8. The breast pump according to claim 1, wherein the milk bowl is provided with a connecting post for being connected to the air pump.

9. The breast pump according to claim 1, wherein the breast shield is flexible.

10. The breast pump according to claim 1, wherein the breast shield is made of silicone.

11. The breast pump according to claim 1, where the flange is a double-layer structure.

12. The breast pump according to claim 1, wherein at least a part of an outer surface of the milk bowl is arranged parallel to an outer surface of the main body.

13. The breast pump according to claim 1, wherein an outer surface of the main body is provided with a connection post for being connected to the air pump and for providing the negative pressure to the membrane.

14. The breast pump according to claim 1, wherein the connecting part protrudes from the milk bowl.

15. The breast pump according to claim 1, wherein the connecting part is ring-shaped.

16. The breast pump according to claim 1, wherein a sealing structure is provided between the connecting part and the membrane so as to prevent the milk from reaching the air pump.

17. The breast pump according to claim 1, wherein a rib is provided between the connecting part and the membrane so as to prevent the milk from reaching the air pump.

18. The breast pump according to claim 1, wherein the positioning structure includes a limiting lug and a limiting groove that limit each other.

19. The breast pump according to claim 1, wherein a one-way valve connected to the airway connector is further disposed in the milk storage cavity, so that the milk flows in one direction to the milk storage cavity from the airway connector.

20. A breast pump, comprising:
a milk bowl,
a breast shield detachably connected to the milk bowl, wherein a milk storage cavity for storing milk is defined by the breast shield and the milk bowl, and the breast shield has a flange shaped to fit a breast and a milk pumping channel for receiving a nipple;
a main body detachably connected to the milk bowl, wherein an air pump for generating negative pressure is provided inside the main body, the milk bowl is air communicated with the negative pressure generated by the air pump, and the negative pressure generated by the air pump acts on the milk pumping channel to promote lactation;
a membrane configured to prevent the milk from reaching the air pump, wherein the milk bowl is provided with a connecting part connected to the membrane, and a rib is provided between the connecting part and the membrane so as to prevent a detachment between the connecting part and the membrane; and
an airway connector disposed in the milk bowl, wherein one side of the airway connector is connected to the milk pumping channel and another side of the airway connector is connected to a milk pumping side of the membrane, and a positioning structure for positioning the airway connector on the milk bowl is provided between the milk bowl and the airway connector, so as to prevent a detachment between the connecting part and the membrane.

21. A breast pump, comprising:
a milk bowl,
a breast shield detachably connected to the milk bowl, wherein a milk storage cavity for storing milk is defined by the breast shield and the milk bowl, and the breast shield has a flange shaped to fit a breast and a milk pumping channel for receiving a nipple;
a main body detachably connected to the milk bowl, wherein an air pump for generating negative pressure is provided inside the main body, the milk bowl is air communicated with the negative pressure generated by the air pump, and the negative pressure generated by the air pump acts on the milk pumping channel to promote lactation;

a membrane configured to prevent the milk from reaching the air pump, wherein an inner surface of the milk bowl is provided with a connecting part connected to the membrane; and a membrane support for installing the membrane, wherein the membrane support and the connecting part jointly define an air-side groove or cavity;

wherein a positioning structure for positioning an airway connector on the milk bowl is provided between the milk bowl and the airway connector, so as to prevent a detachment between the connecting part and the membrane.

* * * * *